(12) United States Patent
Smith et al.

(10) Patent No.: US 7,060,283 B1
(45) Date of Patent: Jun. 13, 2006

(54) IMMUNOREACTIVE PEPTIDES FROM EPSTEIN-BARR VIRUS

(75) Inventors: Richard S. Smith, Del Mar, CA (US); Gary R. Pearson, Great Falls, VA (US); D. Elliot Parks, Del Mar, CA (US); Susan Pothen Varghese, Centerville, VA (US)

(73) Assignees: Ortho Diagnostic Systems, Inc., Raritan, NJ (US); Georgetown Univeristy, Washington, DC (US)

( * ) Notice: Subject to any disclaimer, the term of this patent is extended or adjusted under 35 U.S.C. 154(b) by 0 days.

(21) Appl. No.: 08/392,934

(22) PCT Filed: Sep. 15, 1993

(86) PCT No.: PCT/US93/08699

§ 371 (c)(1),
(2), (4) Date: Oct. 28, 1996

(87) PCT Pub. No.: WO94/06470

PCT Pub. Date: Mar. 31, 1994

Related U.S. Application Data

(63) Continuation-in-part of application No. 07/945,280, filed on Sep. 15, 1992, now abandoned.

(51) Int. Cl.
C07K 14/05 (2006.01)
C07K 4/02 (2006.01)
C07K 14/01 (2006.01)

(52) U.S. Cl. ............... 424/230.1; 530/826; 530/327; 530/324; 530/325; 514/2; 424/186.1; 424/204.1; 424/230.1; 424/192.1; 424/193.1; 424/196.11; 424/199.1; 435/975

(58) Field of Classification Search ............... 514/2, 514/12, 13; 530/826, 326, 327, 324, 325; 424/186.1, 204.1, 230.1, 192.1, 197.1, 196.11, 424/199.1; 435/975
See application file for complete search history.

(56) References Cited

U.S. PATENT DOCUMENTS

| 3,654,090 A | 4/1972 | Schuurs et al. ............ 435/7.93 |
| 3,850,752 A | 11/1974 | Schuurs et al. ............ 435/7.93 |
| 4,016,043 A | 4/1977 | Schuurs et al. ............... 435/5 |
| 4,172,124 A | 10/1979 | Koprowski et al. ...... 435/70.21 |
| 4,196,265 A | 4/1980 | Koprowski et al. ...... 435/70.21 |
| 3,654,090 | 7/1982 | Schuurs et al. ............ 435/7.93 |
| 4,629,783 A | 12/1986 | Cosand ....................... 530/324 |
| 4,879,213 A | 11/1989 | Fox et al. |

FOREIGN PATENT DOCUMENTS

| EP | 017254 | 3/1986 |
| EP | 0 280 813 | 9/1988 |
| WO | 9108224 | 6/1991 |
| WO | WO 94/06470 | 3/1994 |
| WO | 9408597 | 4/1994 |
| WO | WO 94/08597 | 4/1994 |

OTHER PUBLICATIONS

Jackman et al., Vaccine, 17:660–668, 1999.*
Burton et al., "A Large Array of Human Monoclonal Antibodies to Type 1 Human Immunodeficiency Virus from Combinatorial Libraries of Asymptomatic Seropositive Individuals" Proc. Natl. Acad. Sci. USA vol. 88: 10134–10137 (Nov. 1991).
Curtiss, L.K. et al., "Localization of Two Epitopes of Apolipoprotein A–I That are Exposed on Human High Density Lipoproteins Using Monoclonal Antibodies and Synthetic Peptides", J. Biol. Chem., vol. 263, No. 27: 13779–13785 (Sep. 1988).
Diener et al., "Specific Immunosuppression by Immunotoxins Containing Daunomycin" Science vol. 231: 148–150 (Jan. 1986).
Douillard, J.Y. and Hoffman, "Monoclonal Antibodies Specific Immunotherapy of Gastrointestinal Tumors" T. Hybridoma 5 Supp 1: S139–S149 (Jul. 1986).
Eisenlohr et al., "Flanking Sequences Influence the Presentation of an Endogenously Synthesized Peptide to Cytotoxic T Lymphocytes" J. Exp Med. vol. 175: 481–487 (Feb. 1992).
Greiner et al., "Recombinant Interferon Enhances Monoclonal Antibody–Targeting of Carcinoma Lesions in Vivo" Science vol. 235, No. 4791: 895–898 (Feb. 1987).
Henle et al, "Epstein–Barr Virus Diagnostic Tests in Infectious Mononucleosis" Human Pathology vol. 5, No. 5: 551–565 (Sep. 1974).
Henle et al., "Demonstration of Two Distinct Components in the Early Antigen Complex of Epstein–Barr Virus–Infected Cells" Int. J. Cancer vol. 8, No. 3: 272–282 (Nov. 1971).
Herlyn et al., "Anti–Idiotypic Antibodies Bear the Internal Image of a Human Tumor Antigen" Science vol. 232, No. 4746: 100–102 (Apr. 1986).

(Continued)

*Primary Examiner*—Ronald B Schwadron
(74) *Attorney, Agent, or Firm*—Woodcock Washburn LLP

(57) ABSTRACT

Epstein-Barr virus (EBV) specific polypeptides consisting of a series of one to 1000 peptide units selected from the group consisting of peptide units Φ, Γ, Δ and Ω, wherein Φ is 25 amino acids or less and has the formula (αETFTETWNRFITHTEβ) (SEQ ID NO:1), Γ is 25 amino acids or less and has the formula (αGMLEASEGLDGWIHQβ) (SEQ ID NO:2), Δ is 25 amino acids or less and has the formula (αHQQGGWSTLIEDNIβ) (SEQ ID NO:3), Ω is 25 amino acids or less and has the formula (αKQKHPKKVKQAFNPLβ) (SEQ ID NO:4), α and β are each independently from 0 to 5 naturally occurring amino acids, and the polypeptide is capable of binding antibody in a specimen from an individual with Epstein-Barr virus (EBV)-associated disease are disclosed. Also disclosed are the use of these polypeptides for the production of polypeptide-specific antibodies and the diagnosis and treatment of EBV-associated disease.

16 Claims, 7 Drawing Sheets

OTHER PUBLICATIONS

Hinuma, Y. et al., "Immunofluorescence and Herpes–Type Virus Particles in the P3HR–1 Burkitt Lymphoma Cell Line" J. Virol. vol. 1, No. 5: 1045–1051 (Oct. 1967).

Jemmerson, "Effects of Conformation, Amino Acid Sequence, and Carrier Coupling on the Immunological Recognition of Peptide and Protein Antigens" Effects on Immunological Recognition of Peptides in Medicine And Biology, Edited by Zegers, Boiersma, Classen, CRC Press Inc., New York Chapter 16, 213–225 (1995).

Köhler and Milstein, "Continuous Cultures of Fused Cells Secreting Antibody of Predefined Specificity" Nature: vol. 256, No. 5517 495–497 (Aug. 1975).

Lenard, J. et al., "Use of Hydrogen Fluoride in Merrifield Solid–Phase Peptide Synthesis" J. Am. Chem. Soc. vol. 89, No. 1: 181–182 (Jan. 1967).

Luka et al., "A Sensitive Enzyme–Linked Immunosorbent Assay (Elisa) Against the Major EBV–Associated Antigens. I. Correlation between Elisa and Immunofluorescence Titers Using Purified Antigens" J. Immunol. Methods 67: 145–156 (1984).

Merrifield, "Solid Peptide Synthesis. I. The Synthesis of a Tetrapeptide", J. Am. Chem. Soc. 85: 2149–2154 (Jul. 1963).

Oi et al., "Chimeric Antibodies", Bio Techniques vol. 4, No. 3: 214–221 (May/Jun. 1986).

Pearson et al., "Application of Epstein–Barr Virus (EBV) Serology to the Diagnosis of North American Nasopharyngeal Carcinoma" Cancer 51: 260–268 (Jan. 1983).

Smith et al., "Antibodies to an Epstein–Barr Virus Nuclear Antigen Synthetic Peptide in Infectious Mononucleosis" Am. J. Clin. Pathology vol. 92 No. 4: 447–451 (Oct. 1989).

Spira et al., "The Identification of Monoclonal Class Switch Variants by Sib Selection and an Elisa Assay" J. Immunol. Methods 74: 307–315 (1984).

Steplewski et al., "Isolation and Characterization of Anti–Monosialoganglioside Monoclonal Antibody 19–9 Class–Switch Variants" Proc. Natl. Acad. Sci., USA, vol. 82: 8653–8657 (Dec. 1985).

Stewart and Young, "Laboratory Techniques in Solid Phase Peptide Synthesis" Solid Phase Peptides Synthesis (W. H. Freeman & Company, San Francisco, Chapter 2 pp. 27–64 (1969).

Sun et al., "Chimeric Antibodies with 17–1A–Derived Variable and Human Constant Regions" Hybridoma, vol. 5 Supplement 1: S17–S20 (1986).

Sutcliffe et al., "Antibodies That React With Predetermined Sites on Proteins" Science vol. 219, No. 4585: 660–666 (Feb. 1983).

Tainer et al, "The Reactivity of Anti–Peptide Antibodies is a Function of the Atomic Mobility of Sites in a Protein" Nature 312: 127–134 (Nov. 1984).

Wolff et al, "The Use of Monoclonal Anti–Thy$_1$ IgG$_1$ for the Targeting of Liposomes to AKR–A Cells in Vitro and in Vivo" Biochemica et Biophysica Acta, 802: 259–273 (1984).

Young "Epstein–Barr Virus" Encyclopedia of Virology, vol. 1, Edited by Webster and Granoff, Academic Press, 404–416 (1994).

Baer, et al., *Nature* 310:207, 1984, DNA sequence and expression of the B95–8 Epstein–Barr virus genome.

Rhodes, et al., *J. Immunol.*, 143:211, 1985, Human Immune Responses to Synthetic Peptides from the Epstein–Barr Nuclear Antigen.

Dillner, *J. Proc. Natl. Acad. Sci, U.S.A.* 81:652, 184, Antibodies against a synthetic peptide identify the Epstein–Barr virus–determined nuclear antigen.

Lerner, et al., *Nature,* 299:592, 1982, Tapping the immunological repertoire to produce antibodies of predetermined specificity.

Pothen, et al., *Int. J. Cancer,* 49:656, 1991, Human T–Cell Recognition of Epstein–Barr Virus–Induced Replication Antigen Complexes.

Ulaeto, et al., *Europ. J. Immunol,* 18:1689, 1986 In vitro T cell responses to a candidate Epstein–Barr virus vaccine: human CD$+T cell clones specific for the major envelope glycoprotein gp340*.

Pothen, et al., *Int. J. Cancer,* 53:199 (1993), Identification of T– and B–Cell Epitopes Associated with a Restricted Component of the Epstein–Barr Virus–Induced Early Antigen Complex.

Ortho Diagnostic Systems, Inc., ORTHO* Epstein–Barr Virus EA(D+R)–IgG Antibody Elisa Test, Product Code 520025, Draft revised Aug. 20, 1993.

Gull Laboratories, EBV–EA Test, Product No. EA100 1988.

Fox, et al., Synthetic Peptide Derived from the Epstein–Barr Virus Encoded Early Diffuse Antigen (EA–D) Reactive with Human Antibodies, J. of Clinical Laboratory Analysis, 1:140–145 (1987).

G.R. Pearson, et al., "Identification of an Epstein–Barr Virus early gene encoding a second component of the restricted early antigen complex", Virology, vol. 160, Jun. 1987, pp. 151–161.

T.A. Waldmann, "Monoclonal Antibodies in diagnosis and therapy", Science, vol. 252, Jun. 21, 1991, pp. 1657–1662.

* cited by examiner

IMMUNOREACTIVE PEPTIDES FROM EPSTEIN-BARR VIRUS

CROSS REFERENCE TO RELATED APPLICATIONS

This Application is the national phase of PCT/US93/08699, filed Sep. 15, 1993, which is a CIP of U.S. application Ser. No. 07/945,280, filed Sep. 15, 1992, abandoned Jan. 31, 1994.

BACKGROUND OF THE INVENTION

1. Field of the Invention

This invention relates to the diagnosis and therapy of Epstein-Barr virus associated disease. More specifically, these modalities are founded on the discovery of EBV-specific peptides.

2. Description of Related Art

Epstein-Barr virus (EBV) is a human herpesvirus which is endemic in all human populations. Most people are infected with the virus in early childhood and then carry the virus for life. If the initial infection is delayed until adolescence, infectious mononucleosis (IM) frequently results. The virus is also linked with certain kinds of cancer. In the malarial belt of Africa, EBV is a contributory factor in the development of Burkitt's lymphoma and in South-East Asia, the virus is linked to the high incidence of undifferentiated nasopharyngeal carcinomas.

Acute viral infection leads to the production of specific nuclear antigens (termed EBNA-I and EBNA-II), an "early antigen" (EA) complex, viral capsid antigens (VCA), and other associated molecules. The "early antigen complex" consists of the "early antigen-diffuse" (EA-D) and the "early antigen-restricted" (EA-R) antigens, based on their distribution in immunofluorescence assays in the cytoplasm plus nucleus (i.e. diffuse distribution) or in the cytoplasm only (i.e. restricted) and based on their staining appearance in methanol-fixed cells. These EA antigens, with molecular weight 50–55 Kd, 17 Kd, and 85 Kd, respectively, are synthesized during the "lytic" phase of EBV infection and not in transformed lymphoblastoid cells. Antibodies against the early antigens are present during acute EBV infection and then disappear as the virus enters a phase of latency. The reappearance of anti-EA antibodies signals viral reactivation and provides a clue to the possible role of this virus in diseases such as nasopharyngeal carcinoma and Burkitt's lymphoma.

Indirect evidence has suggested a possible role for EBV reactivation in patients with Sjogren's syndrome, an autoimmune disorder characterized by lymphoid infiltrates of the salivary gland (the normal site for EBV latency). Since antibodies to EA antigens are detected by immunofluoreseence assays, such antibodies cannot be detected in patients who possess antinuclear and anticytoplasmic antibodies as part of an autoimmune disease. Therefore it would be desirable to have purified EA molecules to allow measurement of anti-EA antibodies in patients with autoimmune diseases and to more accurately quantitate anti-EA antibodies in other patients with acute or reactivated EBV.

Recently, the DNA sequence of EBV was determined (Baer, et al., Nature 310:207, 1984) and the EA-D antigen localized in the genome. Using a monoclonal antibody directed against the EA-D protein, sufficient protein was purified to allow partial amino acid sequence determination and thus localization of the coding sequences. Using that information, it was possible to prepare a series of synthetic peptides based on the DNA sequence. The same strategy has proved useful in identifying immunologically important epitopes on the EBNA-I antigen (Rhodes, et al., *J. Immunol.*, 134:211, 1985) and the EBNA-II antigens (Dillner, *J. Proc. Natl. Acad. Sci. U.S.A.*, 81:4652, 1984) of EBV. A synthetic peptide derived from the EA-D molecule which contains an epitope reactive with immune human sera from patients with IM and other disease states has also been described (Fox, et al., *J. Clin. Lab. Anal.*, 1:140, 1987).

Recent studies have shown that chemically synthesized polypeptides corresponding to short linear segments of a protein's primary amino acid residue sequence can be used to induce antibodies that immunoreact with the native protein (Lerner, et al., *Nature*, 299:592, 1982; Sutcliffe, et al., *Science*, 219:260, 1983). In addition, some studies have shown that synthetic polypeptides can immunoreact with antibodies induced by native proteins (Rhodes, et al., *J. Immunol.*, 134:211, 1985). Thus, some synthetic polypeptides can immunologically mimic the immunogenic and antigenic determinants of native proteins.

However, as is well known in the art, the application of synthetic peptide technology still suffers several shortcomings. For instance, the identification of peptides capable of mimicking antigenic determinants on a native protein requires knowing the amino acid residue sequence of the protein. Whereas the amino acid residue sequence can be predicted from the nucleic acid sequence of the gene coding for the protein, such a prediction can only be made if the correct reading frame of the gene is known.

The nucleic acid sequence of the EBV genome is known. However, even if a protein's amino acid residue sequence is known, methods for identifying the loci in the protein that constitute the immunogenic and antigenic determinants are experimental in nature and do not yield predictable results. There are at least two reasons for this. First, without knowing a protein's 3-D structure there is no reliable method for determining which linear segments of the protein are accessible to the host's immune system. Second, whether the 3-D structure is known or not, short linear polypeptides often appear not to have the ability to mimic the required secondary and tertiary conformational structures to constitute appropriate immunogenic and antigenic determinants (Tainer, et al., *Nature*, 312:127, 1984). However, methods such as Berzofsky's algorithm (AMPHI program, 1987) have been developed which allow the identification of those dominant epitopes of a molecule that preferentially interact with T or B-cells.

Previous studies have examined the cellular immune response to EBV-induced antigens synthesized during the virus replication cycle (Pothen, et al., *Int. J. Cancer*, 49:656, 1991). The results demonstrated that some of the components of the early antigen (EA) complex were very effective in inducing a strong T-cell proliferative response similar to that previously noted with the major membrane glycoprotein, gp$^{350}$/$_{250}$ (Ulaeto, et al., *Europ. J. Immunol.*, 18:1689, 1988). Both CD4+ and CD8+ lymphocyte populations from EBV-infected donors proliferated in the presence of polypeptides purified from the EA complex by immunoaffinity chromatography. The major polypeptide of EA-D and one of the major polypeptides of EA-R were particularly effective in this T-cell recognition assay. The data suggested that these components of the EA complex might function as important target antigens in the immunosurveillance of EBV-infected or immortalized cells. Identification of the dominant T and B-cell epitopes expressed on EA-R complex polypeptides would provide information on the importance of the antibody responses to these components in the diagnosis and management of individuals with EBV-associated lymphoproliferative diseases.

It would be desirable to develop improved methods to assay for the presence of EA-R or EA-D and anti-EA-R or anti-EA-D antibodies in a body sample so as to allow diagnosis of EBV involvement in disease, as well as diagnosis os the stage of a disease such as infectious mononucleosis. The identification of those B and T-cell epitopes on EA-R/EA-D polypeptides would be an important step toward synthesis of the molecules for use for diagnostic and disease management purposes in individuals with EBV associated lymphoproliferative diseases.

SUMMARY OF THE INVENTION

The present invention provides polypeptides which define immunogenic sites which are specific for Epstein-Barr virus (EBV). These polypeptides can be used for immunodiagnosis and immunotherapy of EBV-associated diseases and to produce monoclonal antibodies which specifically bind to these polypeptides. These monoclonal antibodies can be used to detect antigen comprising the polypeptide of the invention and also used therapeutically to ameliorate EBV-associated disease.

The details of the preferred embodiment of the present invention are set forth in the accompanying drawings and the description below. Once the details of the invention are known, numerous additional innovations and changes will become obvious to one skilled in the art.

DETAILED DESCRIPTION OF THE INVENTION

Figure 1:
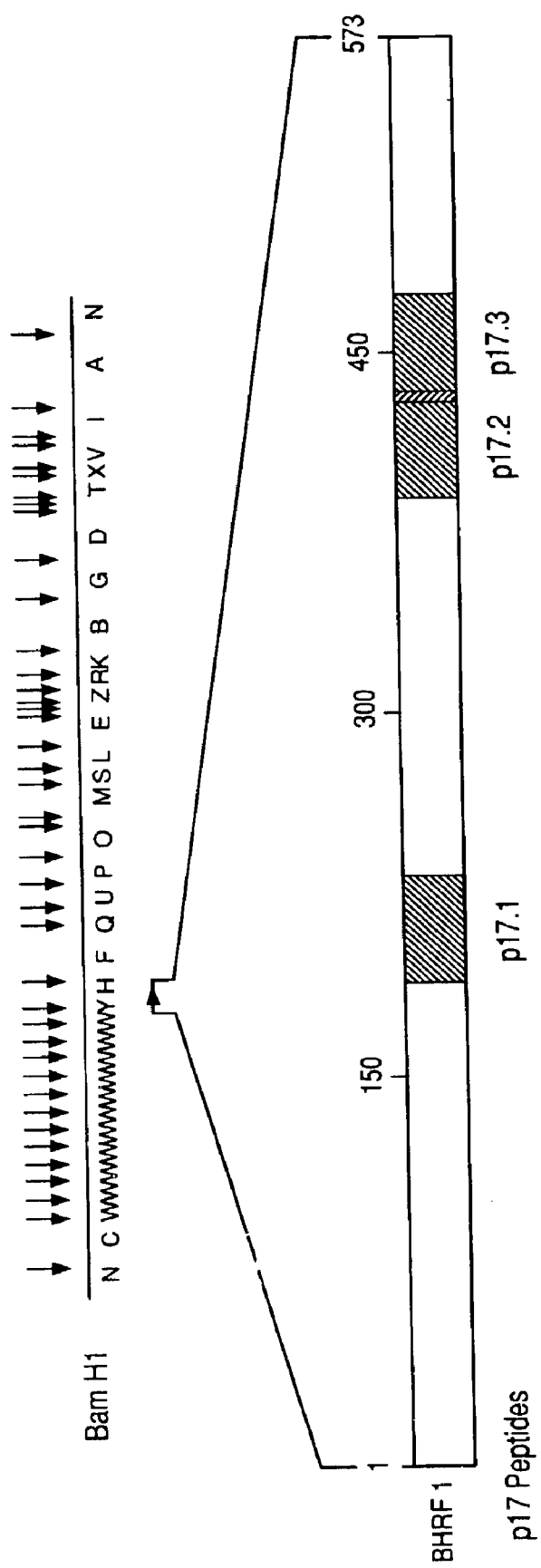
FIG. 1 shows a schematic map of the EBV genome denoting the BamHI HRF1 reading frame and the regions in BHRF1 encoding for the synthetic peptides.

A preferred embodiment of the invention comprises the epitopic polypeptides ETFTETWNRFITHTE (SEQ. I.D. NO. 1), GMLEASEGLDGWIHQ (SEQ. I.D. NO. 2), HQQGGWSTLIEDNIP (SEQ. I.D. NO. 3), KQKHPKKVKQAFNPL (SEQ. I.D. NO. 4), and conservative variations and mixtures of these peptides. The term "conservative variation" as used herein denotes the replacement of an amino acid residue by another, biologically similar residue.

Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide. Thus, by using a routine screening method, such as by testing a conservative variant polypeptide with sera from a patient with EBV-associated disease, one of skill in the art can readily determine if the variant polypeptide has the requisite biological activity of the polypeptide of the invention without resort to undue experimentation.

The epitopic polypeptides of the invention may contain additional amino acids at the amino and carboxy termini in order to increase their serological reactivity. Preferably, the additional amino acids are the naturally occuring amino acids of the protein, on conservative variations of these amino acids, and range in number from about 0 to about 5 independently. For example, a variation of SEQ. I.D. NO. 1 comprises the epitopic polypeptide, QNSETFTETWNRFITHTEHVD, and a variation of SEQ. I.D. NO. 4 comprises the epitopic polypeptide, ARQKQKHPKKVKQAFNPLI, where the underlined amino acids represent extensions of the original polypeptides. The polypeptides of the invention can also be utilized as repeating units ranging from 1 to about 1000 units in length. These units can be homogeneous, for example, where all of the units are repeats of the same polypeptide or can be mixtures of the polypeptides of the invention.

The peptides of the invention can be used singularly, in mixtures, or as multimers such as aggregates, polymers, and the like. Thus, the invention embraces polypeptides which comprise one or more of the same, or different, polypeptides of the invention to produce a homogeneous or heterogeneous polymer with respect to the particular polypeptides of the invention which are contained therein. Appropriate techniques for producing various mixtures, aggregates, multimers and the like will be known to those of skill in the art. For example, the invention includes a polypeptide comprising SEQ. I.D. NO.1 and SEQ. I.D. NO.2, NO.3 or NO.4 or any combination of these, wherein the sequences are linked directly or indirectly, for example, by using a spacer or linker moiety.

Peptides of the invention can be synthesized by such well known solid phase peptide synthesis methods described by Merrifield, *J. Am. Chem. Soc.* 85:2149, 1962, and Stewart and Young, *Solid Phase Peptides Synthesis*, (Freeman, San Francisco, 1969, pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on SEPHADEX G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid-phase Edman degradation.

During or after the synthesis, reactive amino acids may be protected by various blocking groups, for example, cysteines may be blocked by 3,4-dimethylbenzyl (DMB) groups, arginines and histidines by tosyl (TOS) groups, aspartic acid and glutamic acids by benzyl (Bzl) groups, and lysines the 2-chloro-benzyloxycarboxyl (2-CBZ) groups. Other protective blocking groups are well-known, and can be used in the present invention. Those of ordinary skill in the art will know of other techniques for peptide synthesis, or can readily ascertain such techniques, without resorting to undue experimentation.

Alternatively, the polypeptides of the invention can be produced using recombinant techniques commonly known to those of skill in the art (see, for example, *Current Protocols in Molecular Biology,* Ausubel, et al., eds., Wiley Interscience Press, 1989, incorporated herein by reference).

The invention also provides polynucleotides which encode the polypeptides of the invention. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. The invention also includes sequences which are complementary and can hybridize to the polynucleotides which encode the polypeptides of the invention.

The term "EBV-associated disease" means any disease caused, directly or indirectly, by EBV as well as diseases which predispose a patient to infection by EBV. Examples of diseases falling into the former category include infectious mononucleosis, nasopharyngeal carcinoma, and Burkitt's lymphoma. Diseases in the latter category (i.e., those which place the patient at risk of EBV infection) include Sjorgren's syndrome and, generally, any condition that causes a state of immunosuppression or decreased function of the immune system such as patients who receive organ transplants and certain cancer therapies.

The present invention further relates to monoclonal antibodies which are specific for the polypeptides of the invention as well as the diagnostic and therapeutic use of these monoclonal antibodies. This specificity enables the monoclonal antibody, and like monoclonal antibodies with like specificity, to be used to bind the polypeptide of the invention when the polypeptide, or amino acids comprising the polypeptide, are present in specimens or a host, such as a human.

Numerous techniques can be utilized to produce the monoclonal antibodies of the invention without resorting to undue experimentation. To a great extent, the products of such monoclonal antibodies is rendered routine because of the highly defined nature of the polypeptides of the invention. Thus, whether the polypeptides of the invention are used for immunization and/or screening, the very limited number of immunogenic determinants on the polypeptides greatly simplifies the identification of cell lines producing monoclonal antibodies of the invention, for example, by limiting the repertoire of clonal expression possible.

One very useful type of cell line for expression of the monoclonal antibodies of the invention is the hybridoma. The general method used for production of hybridomas producing monoclonal antibody is well known (Kohler and Milstein, *Nature,* 256:495, 1975). The resulting hybridomas were then screened for production of monoclonal antibodies capable of binding to the polypeptides of the invention.

The techniques of sensitization and/or immunization, cell fusion, ascites production, selection of mixed hybridomas, or subcloning of monoclonal hybridomas are generally well known in the art. Attention is directed to Koprowski, et al., U.S. Pat. No. 4,172,124, Koprowski, et al., U.S. Pat. No. 4,196,265, or Douillard, J. Y. and Hoffman, T., *Basic Facts about Hybridomas, in Compendium of Immunology,* Vol. II, L. Schwartz, ed. (1981), which are herein incorporated by reference.

In general, the purified epitopic peptides have a cystine attached at the C-terminus to permit unidirectional attachment of. the synthetic peptide to an immunogenic protein through a connecting bridge, for example, maleimidobenzoylated (MB)-keyhole limpet hemocyanin (KLH). Other immunogenic conjugates can also be used, for example, albumin, and the like. The resulting structure may have several peptide structures linked to one molecule of protein.

Somatic cells derived from a host immunized against the synthetic peptides can be obtained by any suitable immunization technique. The host subject is immunized by administering the antigen, usually in the form of a protein conjugate, as indicated above, by any suitable method, preferably by injection, either intraperitoneally, intravenously, subcutaneously, or by intra-foot pad. Adjuvants may be included in the immunization protocol.

The initial immunization with the protein bound antigen can be followed by several booster injections given periodically at intervals of several weeks. The antibody contained in the plasma of each host can then be tested for its reactivity with the immunizing polypeptide of the invention. The host having the highest response is usually most desirable as the donor of the antibody secreting somatic cells used in the production of hybridomas. Alternatively, hyperimmunization can be effected by repeatedly injecting additional amounts of peptide-protein conjugate by intravenous and/or intraperitoneal route.

The isolation of hybridomas producing monoclonal antibodies of the invention can be accomplished using routine screening techniques which permit determination of the elementary reaction pattern of the monoclonal antibody of interest. Thus, if a monoclonal antibody being tested binds with a polypeptide of the invention, then the antibody being tested and the antibody produced by the hybridomas of the invention are equivalent.

Alternatively, since the invention teaches polypeptides or amino acid sequences which are specifically required for binding of the preferred monoclonal antibodies of the invention, it is now possible to use these peptides for purposes of immunization to produce hybridomas which, in turn, produce monoclonal antibodies specific for the polypeptide. This approach has the added advantage of decreasing the. repertoire of monoclonal antibodies generated by limiting the number of antigenic determinants presented at immunization by the polypeptide. The monoclonal antibodies produced by this method can be screened for specificity using standard techniques, for example, by binding polypeptide to a microtiter plate and measuring binding of the monoclonal antibody by an ELISA assay.

It is also possible to determine, without undue experimentation, if a monoclonal antibody has the same specificity as a monoclonal antibody of the invention by ascertaining whether the former prevents the latter from binding the polypeptide of the invention. If the monoclonal antibody being tested competes with the monoclonal antibody of the invention, as shown by a decrease in binding by the monoclonal antibody of the invention, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the polypeptide of the invention with which it is normally reactive, and then add the monoclonal antibody being tested to determine if the monoclonal antibody being tested is inhibited in its ability to bind the antigen. If the monoclonal antibody being tested is inhibited then, in all likelihood, it has the same, or a closely related, epitopic specificity as the monoclonal antibody of the invention.

While the in vivo use of a monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the EBV-associated disease suppressing efficacy of the donor antibody. One way in which it is possible to circumvent the likelihood of an adverse immune response occurring in the host is by using chimeric antibodies (Sun, et al., *Hybridoma*, 5 (Supplement 1): S17, 1986; Oi, et al., *Bio Techniques*, 4(3): 214, 1986). Chimeric antibodies are antibodies in which the various domains of the antibodies' heavy and light chains are coded for by DNA from more than one species. Typically, a chimeric antibody will comprise the variable domains of the heavy ($V_H$) and light ($V_L$) chains derived from the donor species producing the antibody of desired antigenic speficity, and the variable domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and $V_L$ domains coded for by DNA isolated from a hybridoma of the invention and $C_H$ and $C_L$ domains coded for with DNA isolated from a human leukocyte.

Under certain circumstances, monoclonal antibodies of one isotype might be more preferable than those of another in terms of their diagnostic or therapeutic efficacy. For example, from studies on antibody-medicated cytolysis, it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of target cells. Particular isotypes of a monoclonal antibody can be prepared either directly, by selecting from the initial fusion, or prepared secondarily, from a parental hybridoma secreting a monoclonal antibody of different ieotype by using the sib selection technique to isolate class-switch variants (Steplewski, et al., *Proc. Natl. Acad. Sci., U.S.A.*, 82:8653, 1985; Spira, et al., *J. Immunol. Methods*, 74:307, 1984). Thus, the monoclonal antibodies of the invention would include class-switch variants having specificity for a polypeptide of the invention.

The isolation of other hybridomas secreting monoclonal antibodies with the specificity of the monoclonal antibodies of the invention can also be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibody produced by a single hybridoma which was used to immunize the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody could be used for immunization since the anti-idiotype monoclonal antibody binding domain effectively acts as an antigen.

Especially preferred for in vivo diagnosis and therapy of EBV-associated disease are human monoclonal antibodies. Recent advances in the monoclonal antibody art now make possible the ability to readily produce human monoclonal antibodies by using recombinant cloning techniques. Typically, these techniques utilize lymphocytes from a patient with demonstrated antibody to the antigen of interest followed by the generation of a recombinatorial library from the nucleic acid isolated from these lymphocytes. This library contains an expression vector adapted to allow the cloning of immunoglobulin heavy and light chains in the host ogranism. Individual colonies producing an antibody of desired specificity for a particular antigen are identified, for example, by attaching the aritigens to a solid place and "panning" for the antibody. (See, for example, Burton, et al., *Proc. Natl. Acad. Sci. USA*, 88:10134, 1991, which is incorporated herein by reference).

Thus, one of skill in the art can analogously produce human monoclonal antibodies specific for the peptides of the invention as a matter of routine by generating a recombinatorial library using nudeic add, preferably mRNA, from the lymphocytes of an individual with humoral immunity to EBV and screening the library so produced using the polypeptides of the invention. In light of the highly defined nature of the polypeptides of the invention, each polypeptide will possess few (probably 1 or 2) epitopes and the screening of the library can be done in a simple and highly specific manner without requiring undue experimentation.

The term "antibody" as used in this invention is meant to include intact molecules as well as fragments thereof, such as Fab and F(ab')$_2$, which are capable of binding the epitopic determinant.

The monoclonal antibodies of the invention can be used in any animal in which it is desirable to administer in vitro or in vivo immunodiagnosis or immunotherapy. The term "animal" as used herein is meant to include both humans as well as non-humans.

The monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of an antigen comprising a polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, an antibody specific for a polypeptide of the invention or an antigen comprising a polypeptide of the invention may be detected by the monoclonal antibodies of the invention when present in biological fluids and tissues. Any specimen containing a detectable amount of such antigen can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis. An especially preferred sample is blood.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-lIfe of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{69}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{58}$Fe.

The monoclonal antibodies of the invention can be used in vitro and in vivo to monitor the course of amelioration of EBV-associated disease in an animal. Thus, for example, by measuring the increase or decrease in the number of cells expressing antigen comprising a polypeptide of the invention or changes in the concentration of such antigen present various body fluids, it would be possible to determine whether a particular therapeutic regimen aimed at ameliorating the EBV-associated disease is effective.

The term "ameliorate" denotes a lessening of the detrimental affect of the EBV-associated disease in the animal receiving therapy. The term "therapeutically effective" means that the amount of monoclonal antibody or polypeptide used is of sufficient quantity to ameliorate the EBV-associated disease.

The term "immunogenically effective amount," as used in the invention, that amount of polypeptide which is necessary to induce an ameliorative immune response to the EBV-associated disease, for example, by stimulating the production of antibodies which will bind to an antigen comprising a polypeptide of the invention.

In inducing an immune response to a polypeptide of the invention, the polypeptide can be administered parenterally by injection, rapid infusion, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing polypeptdes of the invention to include an adjuvant. Adjuvants are substances that can be used to non-specifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AIK(SO_4)_2$, $AINa(SO_4)_2$, $AINH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from Mycobacterium tuberculosis, as well as substances found in Corynebacterium parvum, Bordetella pertussis, and members of the genus Brucella).

The physical form of the polypeptide antigen which is used to immunize an animal can be either aggregated or non-aggregated. Aggregated polypeptide can be produced from non-aggregated polypeptide by such common techniques as, for example, treatment with glutaraldehyde or other cross-linking agents. The aggregated polypeptide thus derived could then be used for purposes of producing an EBV-associated disease ameliorating composition effective in inducing an active immune reaction. However, regardless of whether an animal is immunized with aggregated or non-aggregated, both of these forms of polypeptide should cause the production of antibodies to the polypeptide. Thus, it is possible to use these anti-polypeptide antibodies diagnostically as, for example, in a kit to detect the presence of polypeptide in a specimen.

As described above, the polypeptide antigen preparations of the invention can be used to induce the production of antibodies which will bind to epitopic determinants of the polypeptide. A particularly useful method in enhancing the production of antibodies to polypeptide is to first immunize with the polypeptide antigenic preparation of the invention followed by a later immunization. Many different techniques exist for the timing of the immunizations when a multiple immunization regimen is utilized. It is possible to use the antigenic preparation of the invention more than once to increase the levels and diversity of expression of the immunoglobulin repertoire expressed by the immunized animal. Typically, if multiple immunizations are given, they will be spaced one to two months apart. Generally, the dosage of polypeptide administered to an animal will vary depending on such factors as age, condition, sex and extent of disease, if any, and other variables which can be adjusted by one of ordinary skill in the art. The antigenic polypeptide preparations of the invention can be administered as either single or multiple dosages and can vary from about 50 mg to about 500 mg of the polypeptide antigen per dose, more preferably about 50 mg to about 300 mg per dose, most preferably about 100 mg to about 200 mg per dose. The monoclonal antibodies of the invention can also be used, alone or in combination with effector cells (Douillard, et al., *Hybridoma*, 5 (Supp. 1:S139, 1986), for immunotherapy in an animal having EBV-associated disease with epitopes reactive with the monoclonal antibodies of the invention.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs with which can be conjugated to the monoclonal antibodies of the invention include non-proteinaceous as well as proteinaceous drugs. The terms "non-proteinaceous drugs" encompasses compounds which are classically referred to as drugs, for example, mitomycin C, daunorubicin, and vinblastine.

The proteinaceous drugs with which the monoclonal antibodies of the invention can be labeled include immunomodulators and other biological response modifiers. The term "biological response modifiers" is meant to encompass substances which are involved in modifying the immune response, for example, in such manner as to enhance the destruction of an EBV-associated disease cell having an EBV antigen comprising a polypeptide of the invention for which the monoclonal antibodies of the invention are specific. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, and interferon. Interferons with which the monoclonal antibodies of the invention can be labeled include alpha-interferon, beta-interferon, and gamma-interferon and their subtypes.

In using radioisotopically conjugated monoclonal antibodies of the invention for immunotherapy certain isotypes may be more preferable than others depending on such factors as leukocyte distribution as well as isotype stability and emission. If desired, the tumor cell distribution can be evaluated by the in vivo diagnostic techniques described above. Depending on the malignancy some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}$Y, may be preferable. On the other hand, if the malignancy consists of simple target cells, as in the case of leukemia, a short range, high energy alpha emitter, such as $^{212}$Bi, may be preferable, Examples of radioisotopes which can be bound to the monoclonal antibodies of the invention for therapeutic purposes are $^{125}$I, $^{131}$I, $^{90}$Y, $^{67}$Cu, $^{212}$Bi, $^{211}$At, $^{212}$Pb, $^{47}$Sc, $^{109}$pd, and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by Corynebacterium diphtheria which can be used therapeutically. This toxin consists of an alpha and beta subunit which under proper conditions can be separated. The toxic A component can be bound to an antibody and used for site specific delivery to an EBV-antigen bearing cell for which the monoclonal antibodies of the invention are specific. Other therapeutic agents which can be coupled to the monoclonal antibodies of the invention are known, or can be easily ascertained, by those of ordinary skill in the art.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers. Thus, for example, the monoclonal antibodies of the invention can be used in combination with alpha-interferon. This treatment modality enhances monoclonal antibody targeting of EBV-containing cells by increasing the expression of monoclonal antibody reactive antigen (Greiner, et al., *Science*, 235:895, 1987). Alternatively, the monoclonal antibody of the invention could be used, for example, in combination with gamma-interferon to thereby activate and increase the expression of Fc receptors by effector cells which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibody of the invention.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and half-life of the agent.

Using the monoclonal antibodies of the invention, it is possible to design therapies combining all of the characteristics described herein. For example, in a given situation it may be desirable to administer a therapeutic agent, or agents, prior to the administration of the monoclonal antibodies of the invention in combination with effector cells and the same, or different, therapeutic agent or agents. Thus, it may be desirable to treat patients with leukemia or lymphoma by first administering gamma-interferon and interleukin-2 daily for 3 to 5 days, and on day 5 administer the monoclonal antibody of the invention in combination with effector cells as well as gamma-interferon, and interleukin-2.

It is also possible to utilize liposomes with the monoclonal antibodies of the invention in their membrane to specifically deliver the liposome to the area of the EBV-associated disease cell. These liposomes can be produced such that they contain, in addition to the monoclonal antibody, such immunotherapeutic agents as those described above which would then be released at the tumor site (Wolff, et al., *Biochemical et Biophysical Acta*, 802:259, 1984).

The dosage ranges for the administration of the monoclonal antibodies of the invention are those large enough to produce the desired effect in which the symptoms of the EBV-associated disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents lower dosages, comparable to those used for in vivo immunodiagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising a polypeptide, or a monoclonal antibody of the invention, the medicament being used for therapy of EBV-associated disease.

Reactivity of a sample with EA-D, 50.10 peptides or anti-EA-D peptide antibodies is preferably associated with nasopharyngeal carcinoma and infectious mononucleosis. Likewise, reactivity with EA-R, 17.1 peptides or anti-EA-R peptide antibodies is preferably associated with lymphomas.

These specific peptides and their corresponding monoclonal antibodies are particularly useful for detecting the EA-D and EA-R transitions associated with a particular disease state.

The above disclosure generally describes the present invention. A more complete understanding can be obtained by reference to the following specific examples which are provided for purposes of illustration only, and are not intended to limit the scope of the invention.

EXAMPLE 1 SYNTHESIS OF p17 AND p50 POLYPEPTIDES

Potential T cell epitopes on the p17 protein were identified using Berzofsky's algorithm (AMPHI Program) (1987). This algorithm postulates that T-cells preferentially interact with peptides that are amphipathic and which form an alpha helical configuration. Based on these characteristics, candidate epitopes on the p17 and p50 proteins were mapped and were found scattered throughout the molecule. The epitopes with the highest amphipathic scores were synthesized and employed in the studies. Out of 8 predicted epitopes on p17, the 3 with the highest scores were synthesized as 15 amino acid residues based on the nucleotide sequences encoding for these putative epitopes (FIG. 1, Table 1). Peptide synthesis was carried out using the solid phase method of Merrifield (1963) on an Applied Biosystems ABI 430-A automated peptide synthesizer using hydroxybenzotrizole hydrate/dicyclo-hexylcarbodiimide activation as described (Curtiss, L. K., et al., *J. Biol. Chem.*, 263:13779–13785, 1988). The resultant peptide resins were treated with 10% anisole/hydrogen fluoride at −4° C for 1 hour (Lenard, J., et al., *J. Am. Chem. Soc.*, 89:181–182, 1967). The peptide preparations (10 μg per run) were analyzed by HPLC using a VYDAC $C^{18}$ column. The starting buffer contained 0.1% trifluoroacetic acid in water (solvent A) and 0.1% trifluoroacetic acid in acetonitrile (solvent B). The run consisted of a 20–70% gradient increase in solvent B over 20 minutes at 40° C. The separations were monitored at an absorbance of 214 nm. Preparative purification of the peptides employed chromatography on a WATERS AUTO 500 preparative HPLC (50×250-mm VYDAC $C^{18}$ column, 15–20 μm) under the same conditions as described for analytical chromatography. Amino acid compositions of al peptides were determined after hydrolysis with a Beckman 6300 high performance analyzer with internal standards. All peptides were lyophilized and stored under vacuum. Synthesis of p50 polypeptides was performed as described above for p17.

EXAMPLE 2 PROLIFERATIVE RESPONSE OF PBL TO SYNTHETIC PEPTIDES

Cells. The $P_3HR$-1 cell line, established from an African Burkitt's lymphoma (ABL) biopsy, was the source of the native p17 component of the EA-R complex in these experiments (Himuna, Y., et al., *J. Virol.*, 1:1045–1051, 1967). The cells were grown in the presence of RPMI 1640 medium supplemented with 10% heat-inactivated (56° C, 30 minutes) fetal calf serum (FCS), 2 mM L-glutamine and 50 μg per ml gentamycin at 37° C. The cells were passaged every 3–4 days by dilution with fresh medium to a cell concentration of $5\times10^5$ cells per ml.

For antigen production, $P_3HR$-1 cells were activated with 20 ng per ml TPA (12-0-tetradecanoyl-phorbol-13 acetate) and 3 mM sodium butyrate for 48 hours. This procedure generally results in the induction of expression of this antigen in more than 70% of the cells as determined by immunofluorescence (Pearson et al., *Virol.*, 160:151–161, 1987).

ELISA. The ELISA for measuring specific antibodies to p17, p50 or to the synthetic peptides was performed as previously described in detail (Luka et al., *J. Immunol. Methods*, 67:145–156, 1984). Aliquots of different antigen concentrations were diluted in 0.5M $Na_2CO_3$ buffer, pH 9.5, added to wells in polystyrene microtiter plates (Linbro) and the plates incubated overnight at 4° C. Following this incubation period, the plates were washed 5× with Tris-HCl, pH 7.4, containing 0.05% Tween 20, 50 mM NaCl and 100 mg per liter albumin (Sigma) and dried for 20 minutes at room temperature. The plates were screened with different anti-EA-R or EA-D antibody positive human sera and the monoclonal antibody to p17 or p50 to identify the optimal concentration of antigen to be used in the serological studies. Alkaline-phosphatase-labelled goat anti-human IgG (Sigma) or goat anti-mouse IgG (Sigma) was used as the indicator system.

For the testing of human sera for antibodies to native p17, p50 or to the synthetic peptides, sera were diluted 1:10 in ELISA buffer, added in 0.1 ml volumes to wells coated with optimal concentrations of antigen and the plates were incubated for 60 minutes at room temperature. After 4 washes with ELISA buffer, 100 μl of alkaline phosphatase-labelled goat anti-human IgG in ELISA buffer were added to each well and the plates were incubated at room temperature for 1 hour. Following four more washes in buffer, the enzyme reaction was performed by dissolving 1 mg per ml of Sigma

TABLE 1

AMINO ACID SEQUENCE OF SYNTHETIC PEPTIDES
FROM 17 Kd EARLY ANTIGEN (EA-R) REGION
AND 50 Kd EARLY ANTIGEN (EA-D) REGION

| | Peptide | Amino Acid Sequences | Location[a] Genomic | Peptide |
|---|---|---|---|---|
| SEQ ID NO: 1 | p17.1 | ETFTETWNRFITHTE | 54.562–54.604 | 62–76 |
| SEQ ID NO: 2 | p17.2 | GMLEASEGLDGWIHQ | 54.766–54.808 | 130–144 |
| SEQ ID NO: 3 | p17.3 | HQQGGWSTLIEDNIP | 54.805–54.847 | 143–157 |
| SEQ ID NO: 4 | p50.10 | KQKHPKKVKQAFNPL | 81.063–81.108 | — |
| SEQ ID NO: 5 | p17.1[b] | QNSETFTETWNRFITHTEHVD | 54.553–54.613 | 59–79 |
| SEQ ID NO: 6 | p50.10[b] | ARQKQKHPKKVKQAFNPLI | 81.054–81.111 | — |

[a]Location based on the predicted position of nucleotides in the prototype EBV (B95.8) DNA sequence of Baer et al., (Nature, 310:207, 1984).
[b]Extension of p17.1 and p50.10, respectively, by the addition of several amino and carboxy-terminal amino acids.

alkaline phosphatase substrate in 1M diethanolamine buffer, pH 10.4, containing 1 mM $MgCl_2$ and 0.1 mM $ZnCl_2$, and 100 μl of the mixture was then added to each well. The reaction was allowed to proceed for 30 minutes at 37° C and then the plates were screened directly with a microplate reader, TITERTEK MULTISKAN MC (Flow), at 420 nm. Readings above 0.1 which was 2× the background noted with antibody-negative sera were considered positive reactions.

Purification of native p17. Cells expressing p17 were washed twice in phosphate-buffered saline (PBS), resuspended in an extraction buffer containing 0.5% NP-40 and 0.5% sodium deoxycholate in 0.02 M Tris hydrochloride (pH 7.4), 0.15 M NaCl, 1 mM B-mercaptoethanol and 10 mM phenylmethyl-sulfonylfluoride (PMSF) and sonicated for 5 cycles of 20 second each. The extracts were then clarified by centrifugation at 40,000 × g for 60 minutes at 4° C in a Beckman JA-20 rotor and the resultant cell-free supernatant passed over an affinity column prepared with a monoclonal antibody to p17 (Pearson et al., Cancer, 51:260–268, 1983). The column was washed once with 5 volumes of extraction buffer and then once with buffer without detergents before elution of the bound p17 with 3M $MgCl_2$ buffered with 20mM Tris-HCl (ph 7.4). The eluates were tested for specificity by Western blotting and ELISA and titrated for specific antigen activity by ELISA (Luka et al., J. Immunol. Methods, 67:145–156, 1984). The protein concentrations were determined using the Bio-Rad assay. The p17-containing eluates were then dialyzed against 100 volumes of 10 mM Tris-HCl (pH 7.4), 150 mM NaCl followed by dialysis against RPMI 1640 medium containing 10% human A EBV antibody-negative serum. The antigen was aliquoted and stored at −70° C until used in the different immunological assays. (Purification of p50 was performed as described above for p17.)

Proliferation assays. T-cell proliferation assays using the native p17 or p50 polypeptide or the synthetic peptides were performed as previously described in detail (Pothen et al., Int. J. Cancer, 49:656–660, 1991). Briefly, peripheral blood lymphocytes (PBLO from sero-positive donors were isolated on FICOLL-HYPAQUE gradients, washed and resuspended in RPMI 1640 media containing 10% heat-inactivated human $A^+$ serum from a sero-negative donor. Cells ($1\times10^5$ per 0.1 ml) were then added to each well in 96-well, round-bottomed tissue culture plates (Costar, Cambridge, Mass.). The different antigen preparations were added to triplicate wells in 0.1 ml volumes and the plates were incubated at 37° C for 5 days. $^3$H-thymidine (5 Ci per mM) was added at a concentration of 1 μCi per well over the last 4 hours of culture. The cells were then harvested with a multichannel sample harvester and $^3$H-thymidine incorporation was determined using a Beckman Model LS 3801 liquid scintillation counter. Stimulation indices for the test antigens were calculated by dividing the average counts per minute (CPMO for the test antigens by the average CPM of the medium control wells.

PBL from asymptomatic EBV-infected individuals were tested for response to any of the three p17 synthetic peptides (Table 1) by a proliferation assay using lymphocytes previously shown to proliferate in the presence of native p17 (Pothen et al., Int. J. Cancer, 49:656–660, 1991). Different concentrations of the synthetic peptides were incubated with the PBL for 5 days and then proliferation was assayed by the incorporation of $^3$H-thymidine. Results from this initial experiment using PBL from an anti-VCA-positive, anti-EA-positive donor are shown in Table 2. The native p17 purified from activated $P_3HR$-1 cells gave a S.I. of 15.8 in this experiment. At concentrations of 50 and 12.5 μg per ml, the p17.1 peptide also induced significant proliferation responses (S.I.'s of 10.8 and 4.7 respectively). Neither of the other synthetic peptides induced a proliferation response at the concentrations tested. PBL from an EBV antibody-negative individual also did not respond to any of the synthetic peptides.

Figure 2A:
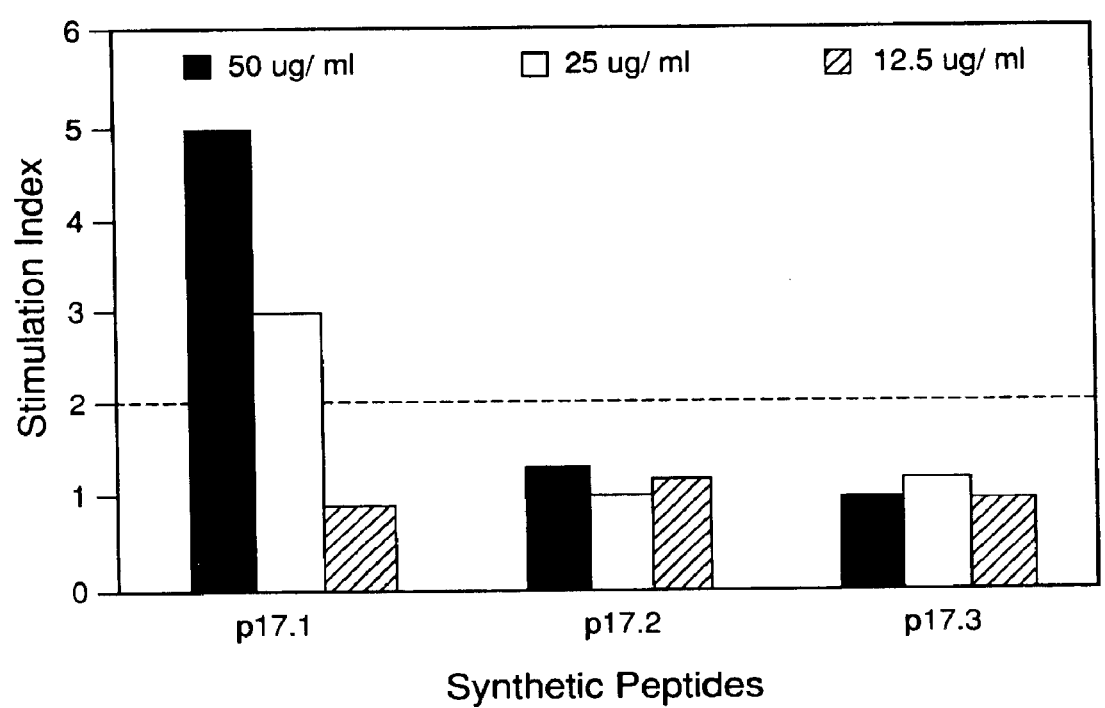
FIGS. 2A, 2B and 2C show the proliferation response of PBL from three anti-VCA-positive, anti-EA-negative individuals (A-C) to different concentrations of the three p17 synthetic peptides.
Figure 2B:
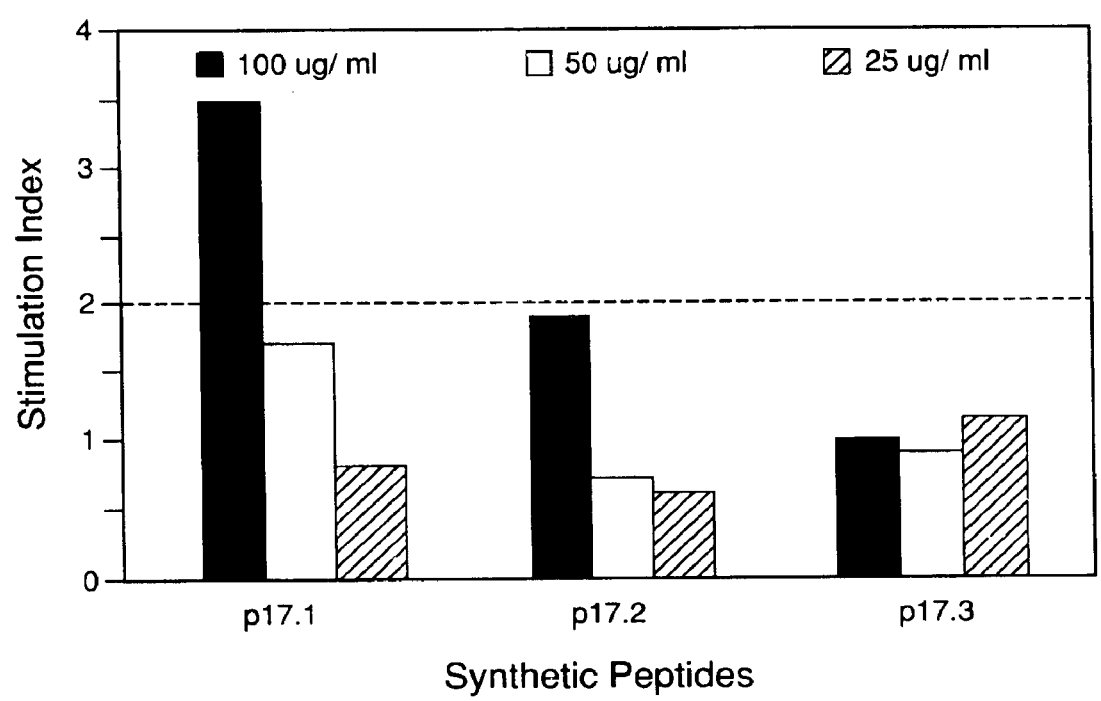
Figure 2C:
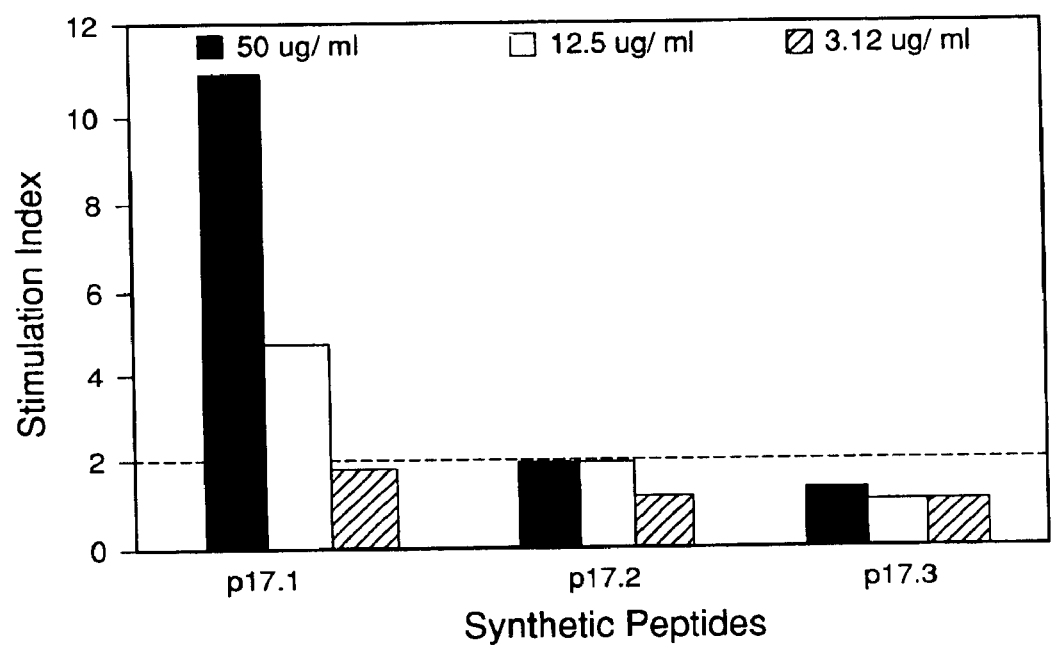

PBL from 3 anti-VCA-positive anti-EA-antibody-negative individuals were also examined in the proliferation assay with the three synthetic peptides. These results are shown in FIGS. 2A, 2B and 2C. Again, all 3 PBL preparations responded to the highest concentrations of p17.1 with S.I.'s ranging from 3.5–11. Two of the preparations (FIGS. 2A, C) also proliferated in the presence of lower concentrations of antigen with S.I.'s of 3 and 5 respectively. None of these PBL preparations proliferated in the presence of p17.2 and p17.3. These experiments established that T-lymphocytes from EBV-infected individuals, irrespective of the presence of antibody to EA, recognized a dominant epitope on p17.

TABLE 2

PROLIFERATION RESPONSE OF PERIPHERAL BLOOD LYMPHOCYTES FROM AN EBV-INFECTED DONOR TO P17 SYNTHETIC PEPTIDES

| Antigen[1] | Concentration (μg/ml) | $^3$H-thymidine Incorporation (cpm + S.D.) | S.I. |
|---|---|---|---|
| — | — | 147 ± 78 | — |
| PHA | 10 | 391567 ± 55800 | — |
| Native p17[2] | 35 | 2327 ± 73 | 15.8 |
| p17.1 | 50 | 1584 ± 37 | 10.8 |
|  | 12.5 | 689 ± 88 | 4.7 |
|  | 3.12 | 263 ± 57 | 1.8 |
| p17.2 | 50 | 277 ± 175 | 1.9 |
|  | 12.5 | 278 ± 58 | 1.9 |
|  | 3.12 | 157 ± 23 | 1.1 |
| p17.3 | 50 | 190 ± 47 | 1.3 |
|  | 12.5 | 132 ± 3 | 0 |
|  | 3.12 | 194 ± 65 | 1.3 |

[1]Antigen was incubated for 5 days with $1 \times 10^5$ lymphocytes. Counts per minute (cpm) ± standard deviation (S.D.) determined from triplicate cultures.
[2]Purified from $P_3HR$-1 cells by immunoaffinity chromatography.

EXAMPLE 2 PROLIFERATIVE RESPONSE OF PBL TO SYNTHETIC PEPTIDES

PBL enriched for T-cell subpopulations were isolated by depleting a particular population by antibody/complement-mediated cytotoxicity. $CD4^+$ cells were prepared by lysing $CD8^+$ cells with anti-CD8 antibody and rabbit complement whereas the $CD8^+$ T cell subpopulation was enriched by lysing $CD4^+$ cells with an anti-CD4 antibody and rabbit complement.

PBL were resuspended in RPMI-1640 medium containing 2 mM L-glutamine, 25 mM HEPES, and 10 μg per ml gentamicin (HEPES media) at a concentration of $20\times10^6$ cells per ml. T cell specific MAb, OKT4 or OKT8 (Ortho Diagnostics Inc.), was added to the cells at the optimal concentration (previously determined by titration to give maximal lysis) and incubated on ice for 30 minutes. The cells were then washed with fresh HEPES media and resuspended at $10\times10^6$ cells per ml in baby rabbit complement (Pel-Freez Clinical Systems) diluted with the HEPES media to the appropriate concentration (previously assayed to give maximal antibody-specific cytotoxicity). The cells were incubated for 45 minutes in a 37° C water bath with gentle mixing every 15 minutes. After incubation, the cells were washed thoroughly with the HEPES media and an aliquot (1–2×10⁶) of cells was removed and stained for flow cytometric analysis which was performed as described below. PBL that were not incubated with either antibody or complement were also processed in parallel for flow cytometry in order to ascertain the original percentage of CD4⁺ and CD8⁺ cells in each donor. The populations that yielded >95% purity and viability were used in proliferation assays.

Proliferation assays using the CD4⁺ or CD8⁺—enriched PBL from the seropositive donors were conducted with varying concentrations of the synthetic peptides as described above. However, in these experiments additional irradiated autologous PBL were used as antigen presenting cells (APC) at a ratio of 5×10⁵ APC to 1×10⁵ CD4⁺ or CD8⁺ cells.

FACS Analysis. The cells removed after incubation above (1–2×10⁶), were stained for 45 minutes at 4° C with 20 µl of the SIMULTEST reagent (Becton-Dickinson) containing fluorescein isothiocyanate conjugated anti-leu 3a (CD4 marker) and phycoerythrin-conjugated anti-leu 2a (CD8 marker). Cells were washed thoroughly, resuspended in RPMI-1640 with 5% FCS and 0.02% sodium azide and analyzed with the cell sorter (FACSTAR Plus, Becton-Dickinson).

Figure 3A:
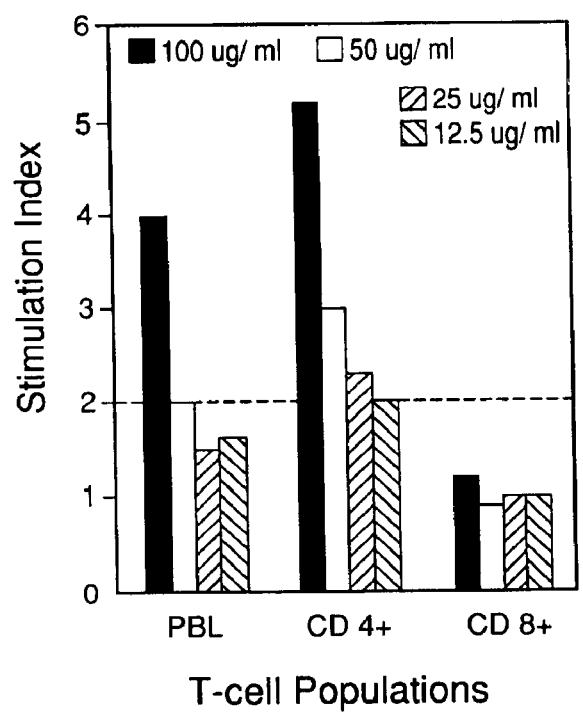
FIGS. 3A and 3B show proliferation response of CD4+ and CD8+ T-cell subpopulations from two donors (A and B) to different concentrations of the synthetic peptide, P17.1.
Figure 3B:
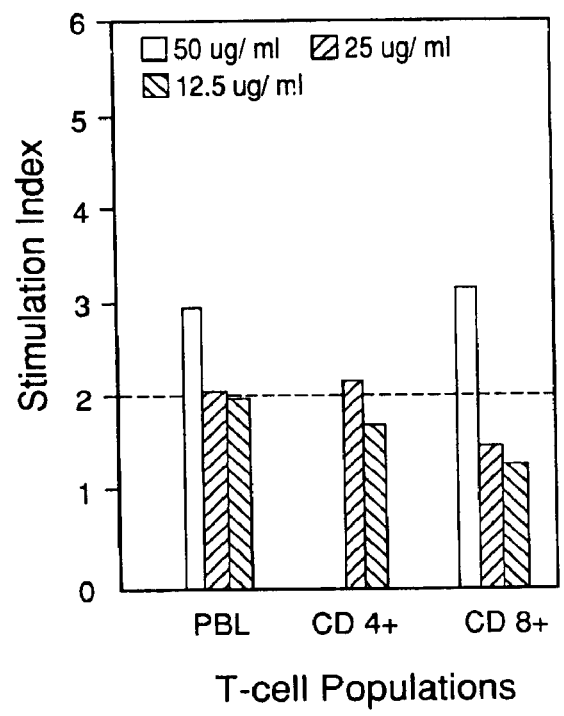

To determine whether both CD4+ and CD8+ T-cell subpopulations were responding to p17.1, lymphocytes from two donors were separated into these two subpopulations which were then employed in the proliferation assay. Results are presented in FIGS. 3A and 3B. The PBL from both donor proliferated in the presence of p 17.1 at the highest concentrations tested in this experiment (100 µg per ml for donor A and 50 µg per ml for donor B). The CD4+ subpopulation from donor A also responded vigorously to different concentrations of p 17.1 with S.I.s as high as 5.3. The CD8+ subpopulation from this donor was unresponsive to this synthetic peptide. This pattern of response was also observed with fractionated CD4+ and CF8+ T-cells from another seropositive donor. In contrast, both the CD4+ and CD8+ T-cell subpopulations from donor B responded to p17.1 with CD8+ subpopulations giving a S.I. of greater than 3 at the highest antigen concentrations tested (50 µg per ml). These results therefore indicated that both CD4+ and CD8+ T-cells recognized this p17 epitope.

EXAMPLE 4 SEROLOGICAL RESPONSE TO p17 SYNTHETIC EPITOPES

Figure 4:
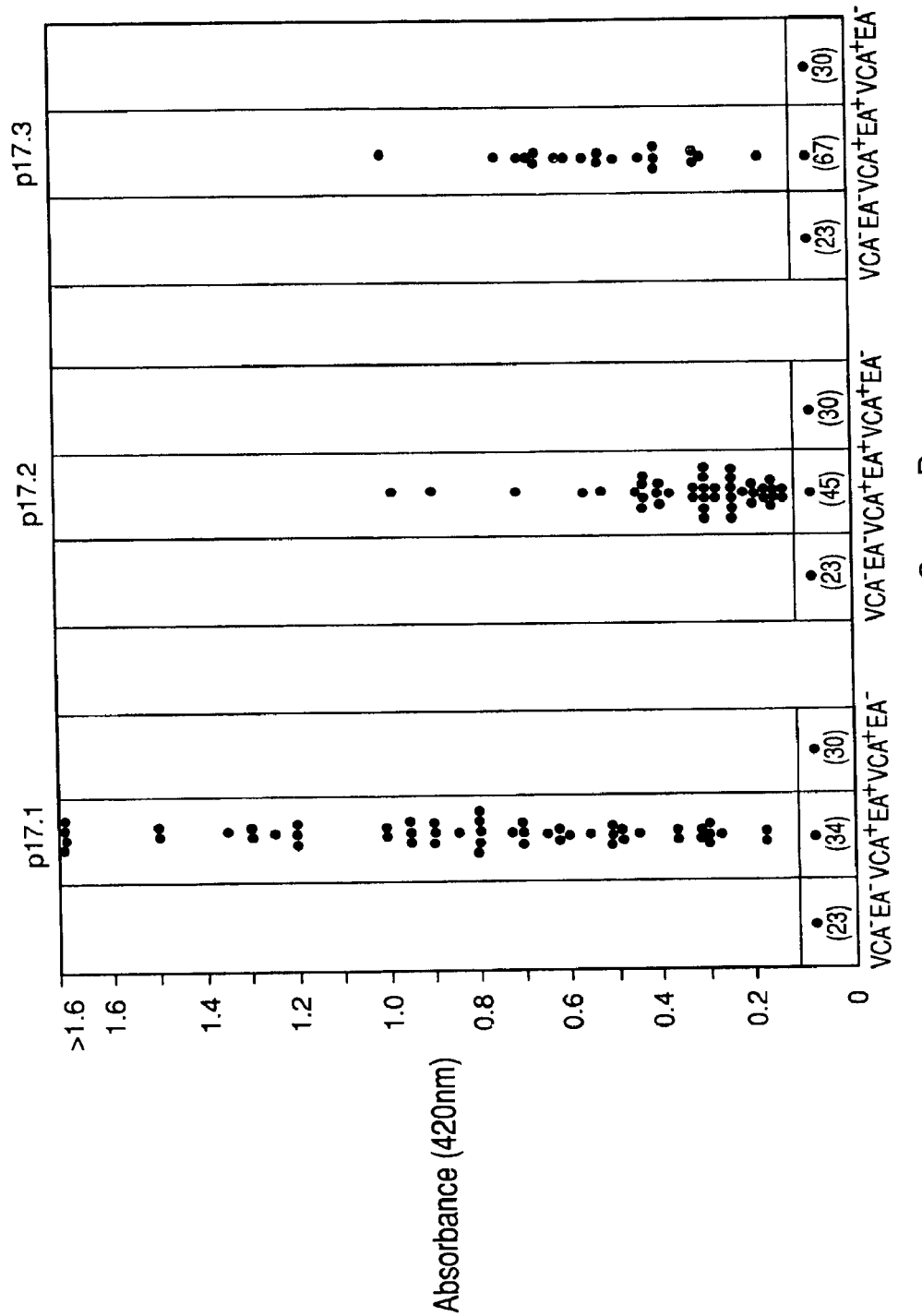
FIG. 4 shows serological reactivity of different sera with the p17 synthetic peptides (17.1, 17.2, 17.3). All sera were tested in the ELISA at 1:10 dilution. Numbers in parenthesis in each column represent number of unreactive sera (absorbance <0.1).

Studies were designed to determine the serological reactivity with the p17 synthetic epitopes. For this purpose, 87 anti-EA antibody-positive sera (titer>160) were tested in the ELISA against optimal pre-determined concentrations (2 µg per well) of the p17 synthetic peptides. The sera were obtained from 28 patients with African Burkitt's lymphoma (ABL) collected during the Ghanian Burkitt Tumor Project, and from 28 North American patients with intermediate large cell, or high grade non-Hodgkin's lymphoma (NANHL). The donors included both HIV-positive and HIV-negative individuals. In addition, sera from 31 North American nasopharyngeal carcinoma (NANPC) patients were examined in this study (Pearson, G. R., et al., *Cancer*, 51:260–268, 1983). To validate the EA specificity of the serological reactions, the results with these sera were compared with results with 23 VCA and EA antibody-negative sera and 30 VCA-antibody-positive, EA-antibody negative sera. Results are shown in FIG. 4. In contrast to the T-cell proliferation results, all three synthetic peptides reacted with the EA antibody-positive sera to varying degrees with p17.1 again being the dominant epitope. Approximately 60% of the anti-EA-positive sera reacted with p17.1, 48% with p17.2 and 23% with p17.3. The anti-EA specificity of these serological results was assured by the lack of reactivity of any of the 53 anti-EA antibody-negative sera with any of the three synthetic peptides. Therefore, these results identified three B-cell epitopes on p17.

Figure 5:
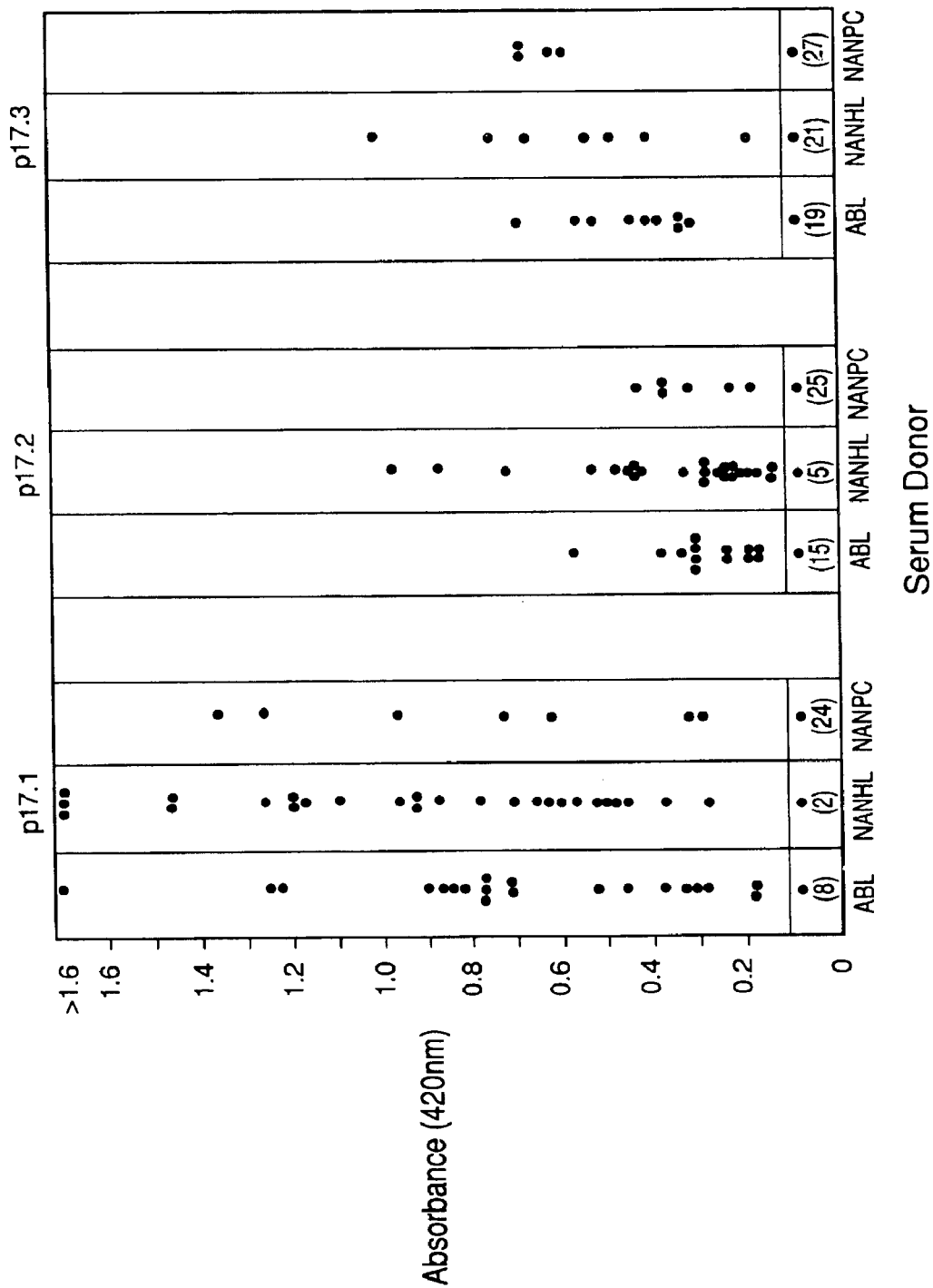
FIG. 5 shows serological reactivity of anti-EA positive sera from different disease categories against the p17 synthetic peptides. All sera were tested at 1:10 dilution. ABL, African Burkitt's lymphoma; NANHL, North American non-Hodgkin's lymphomas including intermediate grade large cell lymphomas, or high grade B cell lymphoma. NANPC, North American nasopharyngeal carcinoma. Numbers in parenthesis in each column represent number of unreactive sera (absorbance <0.1).

To determine why some anti-EA-antibody sera reacted with these synthetic peptides while others did not, the data were analyzed according to the serum donor. These results are presented in FIG. 5. A striking specificity was noted with patients with lymphoproliferative diseases who normally have anti-EA-R antibodies in their sera as opposed to the anti-EA-D-positive NPC. Seventy-one percent of the sera from ABL patients and 93% of the sera from patients with NANHL reacted with p17.1 as opposed to 23% of the sera from North American patients with NPC. A similar specificity was noted with p17.2 and p17.3. These results demonstrated the potential value of one or more of these synthetic polypeptides for measuring anti-EA-R antibodies in the sera of patients with lymphoproliferative diseases and are summarized in Table 3.

TABLE 3

SUMMARY OF SERUM REACTIVITY WITH 17 KD EA-R SYNTHETIC PEPTIDES

| Serum Donors[1] | No. Positive/No. Tested (%) | | |
|---|---|---|---|
| | p17.1 | p17.2 | p17.3 |
| Normal (VCA–EA–) | 0/23 (0) | 0/23 (0) | 0/23 (0) |
| Normal (VCA+EA–) | 0/30 (0) | 0/30 (0) | 0/30 (0) |
| Lymphoma (total) | 46/56 (82) | 36/56 (64) | 16/56 (29) |
| a) Burkitt's lymphoma (African) | 20/28 (71) | 13/28 (46) | 9/28 (32) |
| b) Non-Hodgkin's lymphoma (North American) | 26/28 (93) | 23/28 (82) | 7/28 (25) |
| Nasopharyngeal carcinoma (North American) | 7/31 (23) | 6/31 (19) | 4/31 (13) |

[1]All lymphoma and nasopharyngeal carcinoma serum donors had antibody titers to EA which were >160 as determined by immunofluorescence. These sera also were positive for antibodies to the native 17 Kd EA-R protein purified from P₃HR-1 cells as determined by ELISA.

EXAMPLE 5 p50.10 FROM THE EA-D REGION

The 50 Kd protein found in the EA-D region of EBV contains a dominant epitope called 50.10. This epitope is located on the EBV genome at 81.063 to 81.108, based on the prototype EBV (B95.8) DNA sequence of Baer, et al., supra. (See Table 1, Example 1.) Synthetic peptides were prepared for 50.10 according to the method described in Example 1. The amino acid sequence of the synthetic peptide for this epitope is

The region of the epitope from 81.036–81.078, which includes portion A, underlined above, shows only weak reactivity with infectious mononucleosis (IM) sera, while the region from 81.081–81.120, which contains portion B, shows no reactivity with IM sera. When the entire 50.10 peptide was tested with IM sera, ²⁴⁄₃₂ or 75% of the sera contained EA-D reactive antibody (IgG) (Table 4). In comparison, only ¹²⁄₃₂, or 38% of IM sera tested showed EA-R reactive antibody.

TABLE 4

SCORING EBV IM WITH EA PEPTIDES 17.1 AND 50.1

| SAMPLE NO. | EA-R PEPTIDE 17.1 O.D. | SCORE | EA-D PEPTIDE 50.10 O.D. | SCORE |
|---|---|---|---|---|
| 2241 | 0.282 | − | 0.673 | + |
| 11984 | 0.542 | + | 0.722 | + |
| 12005 | 0.981 | + | 0.441 | − |
| 12288 | 0.700 | + | 0.610 | + |
| 12407 | 0.787 | + | 0.751 | + |
| 12409 | 0.592 | + | 0.609 | + |
| 12418 | 0.463 | − | 0.382 | − |
| 12498 | 0.637 | + | 0.342 | − |
| 12502 | 0.924 | + | 0.270 | − |
| 12587 | 0.571 | + | 0.890 | + |
| 12600 | 0.260 | − | 0.323 | − |
| 12611 | 0.259 | − | 0.436 | − |
| 12801 | 0.601 | + | 0.605 | + |
| 12828 | 0.375 | − | 0.895 | + |
| 12829 | 0.257 | − | 0.652 | + |
| 12836 | 0.692 | + | 0.722 | + |
| 12837 | 0.523 | + | 1.491 | + |
| 12840 | 0.488 | − | 0.723 | + |
| 12888 | 0.423 | − | 0.847 | + |
| 12889 | 0.574 | + | 1.184 | + |
| 12892 | 0.430 | − | 0.634 | + |
| 12893 | 0.592 | + | 0.626 | + |
| 12899 | 0.825 | + | 0.895 | + |
| 12900 | 0.264 | − | 0.498 | − |
| 13075 | 0.154 | − | 0.252 | − |
| 13419 | 0.655 | + | 0.678 | + |
| 13637 | 0.719 | + | 0.886 | + |
| 13769 | 0.757 | + | 1.307 | + |
| 13929 | 0.332 | − | 1.031 | + |
| 14043 | 0.095 | − | 0.631 | + |
| 14128 | 0.434 | − | 0.693 | + |
| 14131 | 0.182 | − | 0.530 | + |
| % Positive | | 12/32 = 38% | | 24/32 = 75% |

Values >0.5 were considered positive (O.D. readings at 420 nm).

Serological reactivity of EA peptides p17.1 and p50.1 which contained additional amino acids on their amino and carboxy termini was tested on EBV IM acute sera which was EA positive. The ELISA results shown in Table 5 indicate that the additional amino acids improved reactivity for both EA peptides.

TABLE 5

COMPARISON OF EA PEPTIDES 17.1 AND 50.1 WITH EXTENSIONS IN EA POSITIVE EBV IM ACUTES

| Sample No. | EA-R 17.1 | 17.1e | EA-D 50.1 | 50.1e |
|---|---|---|---|---|
| 2241 | 0.282 | 1.277 | 0.673 | >2 |
| 12498 | 0.637 | 0.502 | 0.342 | 0.946 |
| 12836 | 0.692 | 1.257 | 0.722 | 1.718 | e = extension as described in Table 1.

EXAMPLE 6 SEROLOGICAL RESULTS WITH p50.10

Serological reactivity of different sera (VCA−EA−, VCA+EA+, VCA+EA−) with the p50.10 synthetic peptide was performed as described in Example 1, according to Pothen, et al., supra. The anti-EA specificity of the serological result was confirmed by lack of reactivity of p50.10. peptide with anti-EA antibody negative sera. Therefore, these results show a B-cell epitope on p50.

Immunofluorescence assays (IFA) were performed as described by Henle, et al. (*Int. J. Cancer*, 8:272–282, 1971).

Western blot analysis was done by methods commonly used in the art (See for example, Coligan, et al., Current Protocols in Immunology, Wiley lnterscience, 1991, Unit 12). Samples of EBV-infected cell lysates ($P_3HR$-1) were tested with human whole antiserum from positive humans (Pearson, et al., *Virology*, 160:151–161, 1987). A comparison was made between EA serology by IFA, using the EA-D 50.1 peptide antisera, and ELISA serology using 50.1 peptide (see Example 2). Samples tested were IM positive and EA-positive by Western blot analysis (50–55K positive reactivity), however, as seen in Table 6, the samples were IFA-EA negative, even at a dilution of 1:10.

TABLE 6

COMPARISON OF EPSTEIN-BARR VIRUS EARLY ANTIGEN (EA) SEROLOGY BY IMMUNOFLUROESCENCE TO THE EA-D 50.1 SYNTHETIC PEPTIDE ELISA[1]

| Sample Number | IFA EA Test | 50.1 ELISA[2] |
|---|---|---|
| 12502 | <10[1] | 0.409 |
| 12840 | <10 | 0.257 |
| 13769 | <10 | 1.034 |

[1]Performed on acute EBV infectious mononucleosis samples (diluted 1:10) that were EA-D Western blot positive
[2]OD reading greater than 0.2 were considered positive.

The serological reactivity of sera from 1) anti-EA-negative, VCA-negative (viral capsid antigen); 2) anti-EA-R positive lymphomas; and 3) anti-EA-D positive, nasopharyngeal carcinomas were studied by ELISA. As seen in Table 7, there is a high correlation between p17.1 reactivity and lymphomas and p50.10 reactivity and nasopharyngeal carcinoma.

TABLE 7

COMPARATIVE REACTIVITY OF ANTI-EA-R AND ANTI-EA-D SERA AGAINST EA-R (P17.1) AND EA-D (P50.10) SYNTHETIC PEPTIDES

| Serum donor | ELISA (420 nm)[1] p17.1 | p50.10 |
|---|---|---|
| Anti-EA-negative (VCA-negative) | 0.071 | 0.089 |
|  | 0.027 | 0.098 |
|  | 0.024 | 0.154 |
|  | 0.041 | 0.086 |
| Anti-EA-R-positive (Lymphomas) | 0.682 | 0.079 |
|  | 1.354 | 0.078 |
|  | 1.793 | 0.098 |
|  | 1.218 | 0.817 |
|  | 1.056 | 0.318 |
|  | 1.104 | 0.095 |
| Anti-EA-D positive (Nasopharyngeal carcinoma) | 0.019 | 1.482 |
|  | 0.014 | 1.573 |
|  | 0.041 | >2.0 |
|  | 0.025 | 1.923 |
|  | 0.265 | 0.944 |
|  | 0.029 | >2.0 |

[1]OD readings at 420 nm; values greater than 0.2 were considered significant.

EXAMPLE 7 DETECTION OF EARLY ANTIGEN D-R TRANSITION

The early antigen D-R transition was followed in a patient during a course of acute infectious mononucleosis. Antibodies to peptides 50.10 (EA-D) and 17.1 (EA-R) were detected by ELISAs on specimens collected over a six month duration. The data in Table 8 show that the antibodies to peptide 50.10 peaked at 62–27–88, while the antibodies to peptide 17.1 peaked at 7–18–88. Therefore, the peptides of the invention are useful for monitoring the course of EBV-associated disease in a patient.

TABLE 8

IgG ELISA: SEQUENTIAL SERA
IgG[1]

| DATE | SERUM NO. | p17.1 | p50.10 |
|---|---|---|---|
| May 26, 1988 | 9817 | 0.158 | 0.104 |
| May 31, 1988 | 9820 | 0.106 | 0.094 |
| Jun. 7, 1988 | 9829 | 0.135 | 0.120 |
| Jun. 20, 1988 | 9941 | 0.169 | 0.147 |
| Jun. 27, 1988 | 9983 | 0.645 | 0.817 |
| Jul. 18, 1988 | 10064 | 0.842 | 0.821 |
| Aug. 29, 1988 | 10237 | 0.260 | 0.561 |
| Sep. 20, 1988 | 10271 | 0.231 | 0.100 |
| Oct. 21, 1988 | 10488 | 0.217 | 0.095 |
| Nov. 15, 1988 | 10546 | 0.193 | 0.140 |

[1]O.D. reading; sera tested at 1.20 dilution: (+) >0.25.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

SUMMARY OF SEQUENCES

Sequence ID No. 1 is the amino acid sequence for the peptide, p17.1, from the 17 Kd early antigen (EA-R) region of EBV Sequence ID No. 2 is the amino acid sequence for the peptide, p17.2, from the 17 Kd early antigen (EA-R) region of EBV Sequence ID No. 3 is the amino acid sequence for the peptide, p17.3, from the 17 Kd early antigen (EA-R) region of EBV Sequence ID No. 4 is the amino acid sequence for the peptide, p50.10, from the 50 Kd early antigen (EA-D) region of EBV Sequence ID No. 5 is a variation of SEQ. ID. No. 1, amino acid sequence for the peptide, p17.1, from the 17 Kd early antigen (EA-R) region of EBV Sequence ID No. 6 is a variation of SEQ. ID. No. 2, the amino acid sequence for the peptide, p17.2, from the 17 Kd early antigen (EA-R) region of EBV Sequence ID No. 7 is the amino acid sequence as described in claim 1

Sequence ID No. 8 is the amino acid sequence as described in claim 1

Sequence ID No. 9 is the amino acid sequence as described in claim 1

Sequence ID No. 10 is the amino acid sequence as described in claim 1

What is claimed is:

1. A polypeptide consisting of an amino acid sequence having the formula:

$$(\varphi)_n$$

wherein n is 1 to about 1000 and φ is 25 amino acids or less and has the formula:

(αETFTETWNRFITHTE β)$_n$ (SEQ. ID NO:1)

wherein α and β are independently from 0 to about 5 naturally occurring amino acids, wherein the polypeptide is capable of binding antibody in a specimen from an individual with Epstein-Barr virus (EBV)-associated disease.

2. A kit useful for the detection of antibody to the polypeptide of claim 1 in a specimen suspected of containing such antibody, the kit comprising carrier means being compartmentalized to receive in close confinement therein one or more containers comprising a container containing the polypeptide of claim 1.

3. The polypeptide of claim 1 wherein φ is QNSETFTETWNRFITHTEHVD (SEQ ID NO:5).

4. The polypeptide of claim 3 wherein n is 1.

5. The polypeptide of claim 1 wherein n is 1.

6. A polypeptide consisting of a series of one to 1000 peptide units selected from the group consisting of peptide units Φ, Γ, Δ and Ω, wherein:

Φ is 25 amino acids or less and has the formula (αETFTETWNRFITETEβ) (SEQ ID NO: 1), Γ is 25 amino acids or less and has the formula (αGMLEASEGLDGWIHQβ) (SEQ ID NO:2), Δ is 25 amino acids or less and has the formula (αHQQGGWSTLIEXDNIPβ) (SEQ ID NO:3), Ω is 25 amino acids or less and has the formula (αKQKHPKKVKQAFNPLβ) (SEQ ID NO:4), α and β are each independently from 0 to 5 naturally occurring amino acids, and the polypeptide is capable of binding antibody in a specimen from an individual with Epstein-Barr virus (EBV)-associated disease.

7. A kit useful for the detection of antibody to the polypeptide capable of binding antibody in a specimen from an individual with Epstein-Barr virus (EBV)-associated disease in a specimen suspected of containing such antibody, the kit comprising carrier means being compartmentalized to receive in close confinement therein one or more containers comprising a container containing the polypeptide of claim 6.

8. The polypeptide of claim 6 consisting of the peptide units Φ and Ω.

9. The polypeptide of claim 8 wherein Φ is (QNSETFTETWNRFITHTEHVD) (SEQ ID NO:5) and Ω is (ARQKQKHPKKVKQAFNPLI) (SEQ ID NO:6).

10. The polypeptide of claim 6 wherein Φ is (QNSETFTETWNRFITHTEHVD) (SEQ ID NO:5) and Ω is (ARQKQKHPKKVKQAFNPLI) (SEQ ID NO:6).

11. The polypeptide of claim 6 wherein Ω is (ARQKQKHPKKVKQAFNPLI) (SEQ ID NO:6).

12. The polypeptide of claim 6 consisting of repeating units of Ω.

13. The polypeptide of claim 12 consisting of a monomer of Ω.

14. The polypeptide of claim 13 wherein Ω is (ARQKQKHPKKVKQAFNPLI) (SEQ ID NO:6).

15. The polypeptide of claim 6, which is homogeneous for one kind of peptide unit selected from the group consisting of Φ, Γ, Δ and Ω.

16. The polypeptide of claim 6, in which the peptide units are mixtures of two to four kinds of peptide units selected from the group consisting of Φ, Γ, Δ and Ω.

* * * * *

UNITED STATES PATENT AND TRADEMARK OFFICE
CERTIFICATE OF CORRECTION

| | |
|---|---|
| PATENT NO. | : 7,060,283 B1 |
| APPLICATION NO. | : 08/392934 |
| DATED | : June 13, 2006 |
| INVENTOR(S) | : Richard S. Smith et al. |

It is certified that error appears in the above-identified patent and that said Letters Patent is hereby corrected as shown below:

<u>Title Page</u>,
Item (56), References Cited,
FOREIGN PATENT DOCUMENTS:
Delete "017254" and insert -- 0173254 --.

OTHER PUBLICATIONS:
Page 2, "Dillner, *J. Proc. Natl. Acad. Sci, U.S.A.*" reference, delete "81:652, 184" and insert -- 81:652 (1984) --.
Page 2, "Ulaeto, et al.," reference, delete "CD$+T" and insert -- CD4+T --.

<u>Title Page</u>,
Item (57), ABSTRACT,
Delete "(αHQQGGWSTLIEDNIβ)" and insert -- (αHQQGGWSTLIEDNIPβ) --.

<u>Column 7</u>,
Line 36, please delete the "speficity," and insert -- specificity, --.

<u>Column 10</u>,
Line 34, delete "half-1Ife" and insert -- half-life --.

<u>Column 17</u>,
Line 16, delete "second" and insert -- seconds --.

<u>Column 18</u>,
Line 45, delete "EXAMPLE 2 PROLIFERATIVE RESPONSE OF PBL TO SYNTHETIC PEPTIDES" and insert -- EXAMPLE 3 FRACTIONATION OF PBL INTO $CD4^+$ and $CD8^+$ SUBPOPULATION --.

<u>Column 19</u>,
Line 30, delete "donor" and insert -- donors --.

UNITED STATES PATENT AND TRADEMARK OFFICE
CERTIFICATE OF CORRECTION

PATENT NO. : 7,060,283 B1
APPLICATION NO. : 08/392934
DATED : June 13, 2006
INVENTOR(S) : Richard S. Smith et al.

It is certified that error appears in the above-identified patent and that said Letters Patent is hereby corrected as shown below:

Column 29,
Line 5, delete "(αETFTETWNRFITETEβ)" and insert
-- (αETFTETWNRFITHTEβ) --.
Line 9, delete "(αHQQGGWSTLIEXDNIPβ)" and insert
-- (αHQQGGWSTLIEDNIPβ) --.

Column 30,
Line 7, delete "(QNSETFETWNRFITHTEHVD)" and insert
-- (QNSETFTETWNRFITHTEHVD) --.

Signed and Sealed this

Fifteenth Day of July, 2008

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<221> NAME/KEY: misc_feature
<223> OTHER INFORMATION: Synthetic Peptide

<400> SEQUENCE: 1

Glu Thr Phe Thr Glu Thr Trp Asn Arg Phe Ile Thr His Thr Glu
1               5                   10                  15

<210> SEQ ID NO 2
<211> LENGTH: 15
<212> TYPE: PRT
<213> ORGANISM: Artificial Sequence
<220> FEATURE:
<221> NAME/KEY: misc_feature
<223> OTHER INFORMATION: Synthetic Peptide

<400> SEQUENCE: 2

Gly Met Leu Glu Ala Ser Glu Gly Leu Asp Gly Trp Ile His Gln
1               5                   10                  15

<210> SEQ ID NO 3
<211> LENGTH: 15
<212> TYPE: PRT
<213> ORGANISM: Artificial Sequence
<220> FEATURE:
<221> NAME/KEY: misc_feature
<223> OTHER INFORMATION: Synthetic Peptide

<400> SEQUENCE: 3

His Gln Gln Gly Gly Trp Ser Thr Leu Ile Glu Asp Asn Ile Pro
1               5                   10                  15
```

```
<210> SEQ ID NO 4
<211> LENGTH: 15
<212> TYPE: PRT
<213> ORGANISM: Artificial Sequence
<220> FEATURE:
<221> NAME/KEY: misc_feature
<223> OTHER INFORMATION: Synthetic Peptide

<400> SEQUENCE: 4

Lys Gln Lys His Pro Lys Lys Val Lys Gln Ala Phe Asn Pro Leu
1               5                   10                  15

<210> SEQ ID NO 5
<211> LENGTH: 21
<212> TYPE: PRT
<213> ORGANISM: Artificial Sequence
<220> FEATURE:
<221> NAME/KEY: misc_feature
<223> OTHER INFORMATION: Synthetic Peptide

<400> SEQUENCE: 5

Gln Asn Ser Glu Thr Phe Thr Glu Thr Trp Asn Arg Phe Ile Thr His
1               5                   10                  15

Thr Glu His Val Asp
            20

<210> SEQ ID NO 6
<211> LENGTH: 19
<212> TYPE: PRT
<213> ORGANISM: Artificial Sequence
<220> FEATURE:
<221> NAME/KEY: misc_feature
<223> OTHER INFORMATION: Synthetic Peptide

<400> SEQUENCE: 6

Ala Arg Gln Lys Gln Lys His Pro Lys Lys Val Lys Gln Ala Phe Asn
1               5                   10                  15

Pro Leu Ile

<210> SEQ ID NO 7
<211> LENGTH: 25
<212> TYPE: PRT
<213> ORGANISM: Artificial Sequence
<220> FEATURE:
<221> NAME/KEY: misc_feature
<223> OTHER INFORMATION: Synthetic Peptide
<221> NAME/KEY: UNSURE
<222> LOCATION: (1)..(5)
<223> OTHER INFORMATION: Xaa is any amino acid
<221> NAME/KEY: UNSURE
<222> LOCATION: (21)..(25)
<223> OTHER INFORMATION: Xaa is any amino acid

<400> SEQUENCE: 7

Xaa Xaa Xaa Xaa Xaa Glu Thr Phe Thr Glu Thr Trp Asn Arg Phe Ile
1               5                   10                  15

Thr His Thr Glu Xaa Xaa Xaa Xaa Xaa
            20                  25

<210> SEQ ID NO 8
<211> LENGTH: 25
<212> TYPE: PRT
<213> ORGANISM: Artificial Sequence
<220> FEATURE:
<221> NAME/KEY: misc_feature
<223> OTHER INFORMATION: Synthetic Peptide
```

-continued

```
<221> NAME/KEY: UNSURE
<222> LOCATION: (1)..(5)
<223> OTHER INFORMATION: Xaa is any amino acid
<221> NAME/KEY: UNSURE
<222> LOCATION: (21)..(25)
<223> OTHER INFORMATION: Xaa is any amino acid

<400> SEQUENCE: 8

Xaa Xaa Xaa Xaa Xaa Gly Met Leu Glu Ala Ser Glu Gly Leu Asp Gly
1               5                   10                  15

Trp Ile His Gln Xaa Xaa Xaa Xaa Xaa
            20                  25

<210> SEQ ID NO 9
<211> LENGTH: 25
<212> TYPE: PRT
<213> ORGANISM: Artificial Sequence
<220> FEATURE:
<221> NAME/KEY: misc_feature
<223> OTHER INFORMATION: Synthetic Peptide
<221> NAME/KEY: UNSURE
<222> LOCATION: (1)..(5)
<223> OTHER INFORMATION: Xaa is any amino acid
<221> NAME/KEY: UNSURE
<222> LOCATION: (21)..(25)
<223> OTHER INFORMATION: Xaa is any amino acid

<400> SEQUENCE: 9

Xaa Xaa Xaa Xaa Xaa His Gln Gln Gly Gly Trp Ser Thr Leu Ile Glu
1               5                   10                  15

Asp Asn Ile Pro Xaa Xaa Xaa Xaa Xaa
            20                  25

<210> SEQ ID NO 10
<211> LENGTH: 25
<212> TYPE: PRT
<213> ORGANISM: Artificial Sequence
<220> FEATURE:
<221> NAME/KEY: misc_feature
<223> OTHER INFORMATION: Synthetic Peptide
<221> NAME/KEY: UNSURE
<222> LOCATION: (1)..(5)
<223> OTHER INFORMATION: Xaa is any amino acid
<221> NAME/KEY: UNSURE
<222> LOCATION: (21)..(25)
<223> OTHER INFORMATION: Xaa is any amino acid

<400> SEQUENCE: 10

Xaa Xaa Xaa Xaa Xaa Lys Gln Lys His Pro Lys Lys Val Lys Gln Ala
1               5                   10                  15

Phe Asn Pro Leu Xaa Xaa Xaa Xaa Xaa
            20                  25
```